United States Patent [19]

Wang et al.

[11] Patent Number: 5,700,753
[45] Date of Patent: Dec. 23, 1997

[54] HETEROGENEOUS BIMETALLIC PALLADIUM-GOLD CATALYST FOR VINYL ACETATE PRODUCTION

[75] Inventors: Tao Wang; Jerry A. Broussard, both of Corpus Christi, Tex.

[73] Assignee: Hoechst Celanese Corporation, Somerville, N.J.

[21] Appl. No.: 655,571

[22] Filed: May 24, 1996

[51] Int. Cl.$^6$ .............................. B01J 23/44; B01J 23/52
[52] U.S. Cl. .......................... 502/330; 502/325; 502/344
[58] Field of Search ................... 502/325, 330, 502/344

[56] References Cited

U.S. PATENT DOCUMENTS

| | | | |
|---|---|---|---|
| 3,275,680 | 9/1966 | Holzrichter | 260/497 |
| 3,743,607 | 7/1973 | Sennewald et al. | 252/430 |
| 3,761,513 | 9/1973 | Sennewald et al. | 260/497 |
| 3,775,342 | 11/1973 | Kronig et al. | 252/430 |
| 3,822,308 | 7/1974 | Kronig et al. | 260/497 |
| 3,939,199 | 2/1976 | Fernholz et al. | 260/469 |
| 3,950,400 | 4/1976 | Fernholz et al. | 260/497 |
| 4,048,096 | 9/1977 | Bissot | 252/430 |
| 4,087,622 | 5/1978 | Nakamura et al. | 560/245 |
| 4,133,962 | 1/1979 | Fernholz et al. | 560/245 |
| 4,902,823 | 2/1990 | Wunder et al. | 560/245 |
| 4,933,204 | 6/1990 | Warren et al. | 427/53.1 |
| 5,179,057 | 1/1993 | Bartley | 502/170 |
| 5,185,308 | 2/1993 | Bartley et al. | 502/170 |
| 5,194,417 | 3/1993 | Smith et al. | 502/330 |
| 5,314,858 | 5/1994 | Colling | 502/330 |
| 5,466,652 | 11/1995 | Paparizos et al. | 502/330 |
| 5,489,522 | 2/1996 | Subramanian et al. | 423/213.5 |
| 5,498,590 | 3/1996 | Burmeister et al. | 502/439 |

*Primary Examiner*—Glenn Caldarola
*Assistant Examiner*—Nadine Preisch
*Attorney, Agent, or Firm*—Donald R. Cassady; M. Susan Spiering

[57] ABSTRACT

This invention provides a heterogeneous bimetallic palladium-gold catalyst for vinyl acetate production from ethylene, acetic acid and oxygen. An invention catalyst is prepared by forming a first shell dispersion coating of colloidal palladium on the catalyst support surface, and super-imposing a second shell dispersion coating of colloidal gold metal on the catalyst support surface. An organometallic gold compound is employed to apply the gold dispersion on the catalyst support surface. The organometallic gold compound does not require a fixing procedure, which normally is the cause of low gold metal retention. A preferred invention palladium-gold catalyst has a high gold metal retention, and exhibits durability and long term selectivity in vinyl acetate production.

19 Claims, No Drawings

HETEROGENEOUS BIMETALLIC PALLADIUM-GOLD CATALYST FOR VINYL ACETATE PRODUCTION

BACKGROUND OF THE INVENTION

A well-known commercial process for the production of vinyl acetate is by the gas phase reaction of ethylene, acetic acid and oxygen in the presence of a supported catalyst which contains palladium.

A preferred type of vinyl acetate catalyst is one having a content of palladium metal and gold metal distributed on the surface of a support substrate such as silica or alumina.

Prior art references which describe supported palladium-gold catalysts for vinyl acetate production include U.S. Pat. Nos. 3,761,513; 3,775,342; 3,822,308; 3,939,199; 4,048,096; 4,087,622; 4,133,962; 4,902,823; 5,194,417; 5,314,858; and references cited therein; incorporated by reference.

The activity and selectivity properties of a supported palladium-gold catalyst are affected by the physicochemical form of the palladium and gold metal content on the catalyst support substrate.

U.S. Pat. No. 4,048,096 describes a catalyst which consists of a palladium-gold alloy distributed as a shell coating on the exterior surface area of a catalyst support such as porous silica. The shell distribution of palladium-gold alloy provides an improved space-time-yield activity in a vapor phase reaction of ethylene, oxygen and a carboxylic acid for vinyl acetate production.

The selectivity of a palladium-gold catalyst in vinyl acetate synthesis also is influenced by the extent and uniformity of the palladium metal and gold metal distribution on the exterior and/or interior surfaces of a porous catalyst support substrate, such as carbon dioxide selectivity and oxygen conversion in an ethylene, oxygen and acetic acid vapor phase reaction.

Accordingly, it is an object of this invention to provide a supported palladium-gold catalyst composition with improved activity and selectivity in vinyl acetate production from ethylene, acetic acid and oxygen.

It is another object of this invention to provide a supported vinyl acetate catalyst which has separately applied shell coatings of dispersed colloidal palladium metal and gold metal.

It is another object of this invention to provide a supported palladium-gold vinyl acetate catalyst which has a high gold retention, and which exhibits durability and long term selectivity in vinyl acetate production from ethylene, acetic acid and oxygen.

It is a further object of this invention to provide a process for preparing a supported vinyl acetate catalyst which has separately applied shell coatings of dispersed colloidal palladium metal and gold metal on the support surface.

Other objects and advantages of the present invention shall become apparent from the accompanying description and examples.

DESCRIPTION OF THE INVENTION

One or more objects of the present invention are accomplished by the provision of a process for the preparation of a catalyst for production of vinyl acetate from ethylene, acetic acid and oxygen, which process comprises (1) forming a precursor catalyst by impregnation of a porous catalyst support medium with a solution of palladium compound, and reduction of the palladium compound to a first shell dispersion coating of colloidal palladium metal on the catalyst support surface; and (2) impregnating the precursor catalyst with an organic solvent solution of organometallic gold compound, and reducing the gold compound to a second shell dispersion coating of colloidal gold metal on the catalyst support surface to form a bimetallic palladium-gold catalyst which provides improved carbon dioxide selectivity and oxygen conversion in vinyl acetate production from ethylene, acetic acid and oxygen.

The catalyst support medium is selected from porous substrates such as silica, alumina, silica/alumina, titania and zirconia, in the form of spheres, tablets, Raschig rings, and the like.

A typical catalyst support medium is illustrated by porous silica spheres which have a radius of 1–8 mm, a pore volume of 0.1–2 cc/g, and an internal surface area of 10–350 m$^2$/g. Commercial catalyst support media are widely available, such a porous 5 mm silica spheres sold under the tradename KA-160 by Sud-Chemie.

In one method of preparing the improved vinyl acetate catalyst of the present invention, the catalyst support first is impregnated with an aqueous solution of a water-soluble palladium compound. Suitable palladium compounds include palladium(II) chloride, palladium(II) nitrate, palladium(II) sulfate, sodium tetrachloropalladium(II), and the like.

The volume of the aqueous impregnating solution preferably is between about 95–100% of the absorptive capacity of the catalyst support.

The impregnated catalyst support is treated with an aqueous solution of a basic alkali metal salt, such as sodium silicate, sodium carbonate or sodium hydroxide. A quantity of basic alkali metal salt is employed which is sufficient to fix the palladium compound onto the catalyst support, i.e., palladium hydroxide is precipitated and is incorporated onto the catalyst support surface.

In another method of catalyst preparation, the catalyst support first is impregnated with an organic solvent solution of at least one organometallic palladium compound. Suitable organometallic compounds include palladium acetylacetonate, palladium acetate, Bis($\eta^3$-Allyl)palladium (II), $\eta^3$-Allyl($\eta^5$-Cyclopentadienyl) palladium(II), $\eta^3$-Allyl (1,5-Cyclooctadiene) palladium(II)tetrafluoroborate, and the like.

Organic solvents which may be employed for the organometallic palladium solution include pentane, hexane, cyclohexane, heptane, octane, isooctane, naphtha, naphthene, benzene, chlorobenzene, nitrobenzene, dichloromethane, and the like.

A significant advantage derives from the use of an organic solution of an organometallic palladium compound instead of an aqueous solution of a water-soluble palladium compound. After impregnation of a catalyst support with a solution of an organometallic palladium compound, no fixing treatment with a basic alkali metal salt is required. The elimination of the noble metal fixing procedure prevents the loss of metal which normally occurs during the fixing treatment and washing steps. A high noble metal loading in a catalyst is essential for optimal activity and selectivity in a vinyl acetate process.

Subsequent to the catalyst support impregnation step with a palladium compound, the catalyst support is treated with a reducing agent to convert the palladium compound into a shell coating of colloidal palladium metal particles on the catalyst support surface. Illustrative of reducing agents are hydrazine, formaldehyde, ethylene, hydrogen, and the like.

The precursor catalyst with a content of pre-reduced palladium metal then is impregnated with an organic solvent solution of at least one organometallic gold compound. Suitable organometallic gold compounds include trimethylsiloxydimethyl gold, trimethylsilylmethyltriphenylphosphine gold, dimethyl gold acetate, gold triacetate, and the like.

Any suitable organic solvent can be employed for the organometallic gold impregnation solution, such as those enumerated above for the organometallic palladium solution.

After the impregnation step, the organometallic gold compound is reduced to a second shell coating of dispersed colloidal gold metal particles on the catalyst support surface. The elimination of the fixing procedure before reduction is particularly significant when introducing colloidal gold metal in a vinyl acetate catalyst. Gold is more difficult to fix with a basic alkali metal salt, such that a fixing procedure causes a low and inconsistent gold retention during the catalyst preparation. The present invention process for vinyl acetate catalyst preparation allows a high and consistent retention of gold in the catalyst composition.

In the invention process for vinyl acetate catalyst preparation, the palladium and gold starting materials are employed in quantities which provide about 1-10 grams of palladium metal and about 1-10 grams of gold metal per liter of finished catalyst.

An invention catalyst can have a palladium metal content between about 0.2-2.5 weight percent, and a gold metal content between about 0.2-2.5 weight percent. The weight ratio of palladium:gold can vary between about 0.5-10:1.

Optionally, the present invention process for catalyst preparation can include an additional procedure to enhance the selectivity of the catalyst in vinyl acetate production. The palladium-gold catalyst obtained by the above-described process is treated with an aqueous solution of alkali metal acetate such as potassium acetate, and then dried. The alkali metal acetate content can be in the range between about 2-10 weight percent, based on the weight of the finished catalyst.

Important advantages of the present invention are achieved by the provision of a heterogeneous bimetallic palladium-gold catalyst composition for the preparation of vinyl acetate from ethylene, acetic acid and oxygen, wherein the catalyst composition comprises a porous catalyst support medium which contains a first shell dispersion coating of colloidal palladium metal on the catalyst support surface, and contains a second shell dispersion coating of colloidal gold metal on the catalyst support surface.

Typically a present invention catalyst is employed in a vinyl acetate process by contacting ethylene, acetic acid and oxygen or air with a catalyst at temperatures between about 100°-200° C. and a pressure between about 1-10 atmospheres. The reaction usually is conducted with an excess of ethylene.

A preferred present invention catalyst is characterized by a high level of palladium metal and gold metal retention, and exhibits durability and improved long term selectivity in vinyl acetate production from ethylene, acetic acid and oxygen.

A present invention catalyst can provide efficient production of vinyl acetate, with a lower yield of carbon dioxide than conventional Bayer vinyl acetate catalysts of the type described in G.B. 1,246,015; incorporated herein by reference.

The following examples are further illustrative of the present invention. The components and specific ingredients are presented as being typical, and various modifications can be derived in view of the foregoing disclosure within the scope of the invention.

The palladium-gold catalysts in the Examples were prepared with different combinations and proportions of palladium and gold starting materials, and compared with Bayer-type palladium-gold catalysts in the production of vinyl acetate from ethylene, acetic acid and oxygen.

Palladium-gold catalysts were prepared from $Na_2PdCl_4$/ $Au(OAc)_3$ (OAc=acetate) on silica, as illustrated by Catalysts A–E in the Examples.

Palladium-gold catalysts were prepared from $Na_2PdCl_4$/ $Ph_3PAuCH_2SiMe_3$ on silica, as illustrated by Catalyst F and Catalyst G in the Examples.

Palladium-gold catalysts were prepared from $Na_2PdCl_4$/ $Me_2AuOSiMe_3$ on silica, as illustrated by Catalyst H and Catalyst I in the Examples.

The Vinyl Acetate Stirred Tank Reactor (VAST) Unit in the Examples is a Berty reactor, or a continuous stirred tank reactor of the recirculating type that is run at constant oxygen conversion (about 45%). The catalyst (62 cc) is loaded in a basket in the reactor, a measured amount of acetic acid, ethylene, and oxygen is added in a nitrogen diluent, and the reactor is brought up to temperature by means of a heating mantle, and the temperature is measured above and below the catalyst. The reaction is terminated after approximately 18 hours at a temperature at which 45% oxygen conversion is maintained. Products are measured by gas-phase chromatography. $CO_2$ selectivities tend to be a little higher for the same catalyst when tested in the VAST Unit compared to the VAMU since the product vinyl acetate is recirculated in contact with the catalyst during the reaction sequence.

The Vinyl Acetate Micro Unit (VAMU) reactor in the Examples is a plug flow type run at constant temperature. The VAMU reactor is a 3 ft-long, 16 mm i.d. stainless steel tube with a 3 mm concentric thermocouple well. The reactor is equipped with a heating jacket through which hot water and steam are circulated. A 30 cc sample of catalyst is diluted with support up to 150 cc and loaded to the reactor. The catalyst/support mixture is topped with 30 cc of support. After a single pass-through of the oxygen, ethylene and acetic acid in a nitrogen diluent, at either constant temperature or constant oxygen conversion, the products are analyzed by gas-phase chromatography.

EXAMPLE I

This Example illustrates the preparation of gold(III) triacetate in accordance with U.S. Pat. No. 4,933,204.

Gold hydroxide [$Au(OH)_3$] was made by heating $HAuCl_4$ in aqueous $Na_2CO_3$ at a pH of 8 for three hours. The resulting red solution was filtered, and the $Au(OH)_3$ precipitate was washed with water, and air-dried. The $Au(OH)_3$ was dissolved in glacial acetic acid with warming to form a solution of gold triacetate.

EXAMPLE II

This Example illustrates the preparation of a pre-reduced palladium on silica composition from $Na_2PdCl_4$, which is employed as an intermediate in the synthesis of present invention palladium-gold type catalysts.

A 250 cc quantity of 5 mm silica spheres (KA-160, Sud Chemie) was impregnated with 82.5 mL of aqueous $Na_2PdCl_4$ (7g Pd/L support) to incipient wetness. The impregnated support was treated with 283 cc of aqueous NaOH (50% w/w NaOH/H$_2$O; 120% of amount needed to convert the metal salt to the hydroxide form). The fixed support was rotated in a Rotovap for 2.5 hours at about 5 rpm.

After fixing, the treated carriers were continually washed with distilled water to remove chloride ions until the wash effluent tested negative with silver nitrate. The water flow rate was about 200 cc/min for each washing. The carriers from each set were dried under a continuous nitrogen flow at a temperature of about 150° C. The dried support was reduced with 5% ethylene in nitrogen at 150° C. for 5 hours.

EXAMPLE III

This Example illustrates the preparation of present invention Pd—Au catalysts, and the properties of the invention catalysts in the production of vinyl acetate from ethylene, acetic acid and oxygen in VAST and VAMU systems in comparison to Bayer Pd—Au catalysts.

Catalyst A

A 0.88 g quantity of Au(OH)$_3$ in 35 mL of acetic acid in a reaction flask was heated at 60° C. for 2 hours to produce a clear reddish-brown solution of Au(OAc)$_3$. A 35 mL quantity of the solution was added to 100 mL of pre-reduced Pd on silica (Example II) at 60° C. in a reaction flask, and the impregnation was conducted for about 30 minutes. The solvent medium was removed at 60° C. under vacuum. The treated silica support was reduced with 5% ethylene in nitrogen at 120° C. for 5 hours. The resulting catalyst was impregnated with 4 g of KOAc in 33 mL of water, and then dried in a fluid bed drier at 100° C. for one hour to provide Pd—Au Catalyst A.

Catalyst B

The procedure of Catalyst A was followed, except that 0.69 g of Au(OH)$_3$ in 38 mL of acetic acid was employed, to provide Pd—Au catalyst B.

Catalyst C

The procedure of Catalyst A was followed, except that 0.5 g of Au(OH)$_3$ in 35 mL of acetic acid was employed, to provide Pd—Au Catalyst C.

Catalyst C

The procedure of Catalyst A was followed, except that 0.25 of Au(OH)$_3$ in 35 mL of acetic acid was employed, to provide Pd—Au Catalyst D.

Catalyst E

The procedure of Catalyst A was followed, except that 0.88 g of Au(OH)$_3$ in 17 mL of acetic acid, and 45 mL of pre-reduced Pd on silica (Example II), were employed to provide Pd—Au Catalyst E.

Catalysts A–D were tested in a VAST system in comparison with Bayer Pd—Au catalysts for the production of vinyl acetate from ethylene, acetic acid and oxygen.

The comparative data are summarized in Table I. In Catalysts A–D, the activity increased as the gold to palladium ratio increased. Catalysts A–D tended to produce less $CO_2$ than the Bayer catalysts. Catalyst A had improved $CO_2$ selectivity (8.7 vs. 9.5), higher activity (2.23 vs. 1.37), and lower EtOAc (0.054 vs. 0.06) than the Bayer commercial catalyst.

Catalysts A–E were tested in a VAMU system in comparison with a Bayer Pd—Au catalyst for the production of vinyl acetate.

In order to evaluate catalyst activity, a midpoint shell temperature of the unit was recorded at a fixed oxygen conversion (about 45%). Lower shell temperatures are an indication of a higher catalyst activity at a constant oxygen consumption.

The comparative data are summarized in Table II. Catalysts D and E exhibited higher $CO_2$ selectivity and lower catalyst activity than Catalysts A–C. Catalysts A–C had improved $CO_2$ selectivity and higher catalyst activity than the Bayer Pd—Au catalyst.

SEM-EDX x-ray mapping indicated that Catalysts A–E had the palladium metal dispersed as a shell coating on the outer surface of the silica support. The gold metal was dispersed mainly on the outer surface of the silica support as a second shell coating, and a lesser proportion of the gold metal was dispersed on the interior pore surface of the silica support.

TABLE I

VAST Unit Data For Pd/Au Catalysts Prepared From Na$_2$PdCl$_4$/Au(OAc)$_3$

| Catalyst | $CO_2$ Selectivity | Heavy Ends | EtOAc | Catalyst Activity |
|---|---|---|---|---|
| Bayer | 9.51 | 0.89 | 0.06 | 1.37 |
| Catalyst A Na$_2$PdCl$_4$, Au(OAc)$_3$ | 8.70 | 1.259 | 0.054 | 2.23 |
| Catalyst B Na$_2$PdCl$_4$, Au(OAc)$_3$ | 8.66 | 1.310 | 0.048 | 2.14 |
| Catalyst C Na$_2$PdCl$_4$, Au(OAc)$_3$ | 8.57 | 1.249 | 0.056 | 2.01 |
| Catalyst D Na$_2$PdCl$_4$, Au(OAc)$_3$ | 8.90 | 0.892 | 0.078 | 1.70 |

TABLE II

VAMU Unit Performance Data For Pd/Au Catalysts Prepared from Na$_2$PdCl$_4$/Au(OAc)$_3$

| Catalyst | Metal Loading | $CO_2$ Selectivity | Heavy Ends | Shell Temperature | $O_2$ Conversion |
|---|---|---|---|---|---|
| Bayer | | 6.54 | 0.652 | 153.9 | 45.3 |
| Catalyst A Na$_2$PdCl$_4$, Au(OAc)$_3$ | Pd: 0.93 Au: 0.39 | 5.63 | 0.761 | 140.9 | 45.6 |
| Catalyst B Na$_2$PdCl$_4$, Au(OAc)$_3$ | Pd: 1.05 Au: 0.31 | 5.89 | 0.729 | 144.5 | 45.5 |
| Catalyst C Na$_4$PdCl$_4$, Au(OAc)$_3$ | Pd: 1.01 Au: 0.25 | 5.89 | 0.648 | 144.4 | 45.0 |

TABLE II-continued

VAMU Unit Performance Data For Pd/Au Catalysts Prepared from Na₂PdCl₄/Au(OAc)₃

| Catalyst | Metal Loading | $CO_2$ Selectivity | Heavy Ends | Shell Temperature | $O_2$ Conversion |
|---|---|---|---|---|---|
| Catalyst D Na₂PdCl₄, Au(OAc)₃ | Pd: 0.97 Au: 0.14 | 6.63 | 0.557 | 149.2 | 44.9 |
| Catalyst E Na₂PdCl₄, Au(OAc) | Pd: 1.00 Au: 1.11 | 6.43 | 0.76 | 146.0 | 45.8 |

EXAMPLE IV

This Example illustrates the preparation of present invention Pd—Au catalysts, and the properties of the invention catalysts in the production of vinyl acetate from ethylene, acetic acid and oxygen in VAST and VAMU systems in comparison to Bayer Pd—Au catalysts.

Catalyst F and Catalyst G

A 34 mL $CH_2Cl_2$ solution of $Ph_3PAuCH_2SiMe_3$ (1 g) was added to 90 mL of pre-reduced palladium on silica (Example II) in a reaction flask, and the impregnation was conducted for about 30 minutes. The solvent medium was removed under vacuum. The treated silica support was reduced with 5% ethylene in nitrogen at 120° C. for five hours. The resulting catalyst was washed with toluene, and dried at 120° C. under vacuum for about 16 hours. The catalyst was impregnated with 3.8 g of KOAc in 30 mL of water, and then dried in a fluid bed drier at 100° C. for one hour to provide Pd—Au Catalyst F. Catalyst G was prepared in the same manner.

Catalyst H

A 16 mL hexane solution of $Me_2AuOSiMe_3$ (0.38 g) was added to 45 mL of pre-reduced Pd on silica (Example II) in a reaction flask, and the impregnation was conducted for about 30 minutes. The solvent medium was removed under vacuum. The treated silica support was reduced with 5% ethylene in nitrogen at 120° C. for five hours. The resulting catalyst was impregnated with 1.8 g of KOAc in 15 mL of water, and then dried in a fluid bed drier at 100° C. for one hour to provide Pd—Au Catalyst H.

Catalyst I

The procedure of Catalyst H was followed, except that a 32 mL hexane solution of $Me_2AuOSiMe_3$ (0.85 g), and 90 mL of pre-reduced Pd on silica (Example II), were employed to provide Pd—Au Catalyst I.

Catalysts F-I were tested in a VAMU system in comparison with a Bayer Pd—Au catalyst for the production of vinyl acetate.

The comparative data are summarized in Table III. Catalysts F-I exhibited improved $CO_2$ selectivity over the Bayer catalyst. Catalyst I had a much lower shell temperature (higher catalyst activity) than the Bayer catalyst. Catalysts H-I had a high gold metal retention of 86% and 98%, respectively. Catalysts F-G and G had a 52% and 57% gold retention, respectively. Catalysts F and I were tested in a VAST system in comparison with Bayer Pd/Au catalysts for the production of vinyl acetate.

The comparative data are summarized in Table IV. Catalysts F and I had improved $CO_2$ selectivity and higher catalyst activity than the Bayer catalyst.

SEM-EDX X-ray mapping indicated that Catalyst I had a Pd—Au shell dispersion of metals on the silica outer surface. Catalyst F had the palladium metal dispersed as a shell coating on the silica outer surface. The gold metal was dispersed mainly on the outer surface of the silica support as a second shell coating, and a lesser proportion of the gold metal was dispersed on the interior pore surface of the silica support.

Catalyst G was tested in a VAMU system continuously over a period of 7 days for the production of vinyl acetate. The extended test period was to monitor the catalyst durability, and the long term selectivity of the invention catalyst. The data was recorded every 24 hours.

The data are summarized in Table V. The data indicated that present invention Catalyst G had long term catalyst durability and selectivity.

TABLE III

VAMU Unit Data For Na₂PdCl₄/Ph₃PAuCH₂SiMe₃ And Na₂PdCl₄/Me₂AuOSiMe3 Catalysts

| Description | Analysis | $CO_2$ Selectivity | Heavy Ends | Shell Temperature | $O_2$ Conversion |
|---|---|---|---|---|---|
| Bayer | | 6.54 | 0.682 | 153.9 | 45.3 |
| Catalyst F Na₂PdCl₄, Ph₃PAuCH₂SiMe₃ | Pd: 1.01 Au: 0.35 | 6.05 | 0.730 | 147.1 | 45.8 |
| Catalyst G Na₂PdCl₄, Ph₃PAuCH₂SiMe₃ | Pd: 1.02 Au: 0.39 | 6.53 | 0.880 | 144.0 | 45.3 |

TABLE III-continued

VAMU Unit Data For $Na_2PdCl_4/Ph_3PAuCH_2SiMe_3$ And $Na_2PdCl_4/Me_2AuOSiMe3$ Catalysts

| Sample Description | Analysis | $CO_2$ Selectivity | Heavy Ends | Shell Temperature | $O_2$ Conversion |
|---|---|---|---|---|---|
| Catalyst H $Na_2PdCl_4$, $Me_2AuOSiMe_3$ | Pd: 0.97 Au: 0.77 | 6.26 | 0.688 | 149.7 | 45.6 |
| Catalyst I $Na_2PdCl_4$, $Me_2AuOSiMe_3$ | Pd: 1.08 Au: 0.94 | 6.13 | 0.915 | 138.5 | 45.0 |

TABLE IV

VAST Unit Data For $Na_2PdCl_4/Ph_3PAuCH_2SiMe_3$ And $Na_2PdCl_4/Me_2AuOSiMe_3$ Catalysts

| Sample Catalyst | $CO_2$ Selectivity | Heavy Ends | EtOAc | Catalyst Activity |
|---|---|---|---|---|
| Bayer | 9.51 | 0.89 | 0.060 | 1.37 |
| Catalyst F $Na_2PdCl_4$, $Ph_3PAuCH_2SiMe_3$ | 8.31 | 1.34 | 0.054 | 1.97 |
| Catalyst I $Na_2PdCl_4$, $Me_2AuOSiMe_3$ | 9.25 | 1.75 | 0.029 | 2.29 |

TABLE V

VAMU Unit Data For $Na_2PdCl_4/Ph_3PAuCH_2SiMe_3$ Over A 7-Day Test Period

| Sample Description | Hours | $CO_2$ Selectivity | Heavy Ends | Shell Temperature | $O_2$ Conversion |
|---|---|---|---|---|---|
| Bayer | | 6.54 | 0.682 | 153.9 | 45.3 |
| Catalyst G $Na_2PdCl_4$, $Ph_3PAuCH_2SiMe_3$ | 24 | 6.53 | 0.88 | 144.0 | 45.3 |
| Catayst G | 48 | 6.59 | 0.91 | 144.0 | 45.4 |
| Catalyst G | 72 | 6.24 | 0.84 | 145.5 | 45.4 |
| Catalyst G | 96 | 6.48 | 0.941 | 145.2 | 45.1 |
| Catalyst G | 120 | 6.07 | 0.817 | 146.5 | 45.7 |
| Catalyst G | 144 | 6.15 | 0.824 | 147.3 | 45.3 |
| Catalyst G | 168 | 6.15 | 0.828 | 148.2 | 45.3 |

What is claimed is:

1. A process for the preparation of a catalyst for production of vinyl acetate from ethylene, acetic acid and oxygen, which process comprises (1) forming a precursor catalyst by impregnation of a porous catalyst support medium with a solution of palladium compound, and reduction of the palladium compound to a first shell dispersion coating of colloidal palladium metal on the catalyst support surface; and (2) impregnating the precursor catalyst with an organic solvent solution of organometallic gold compound, and reducing the gold compound to a second shell dispersion coating of colloidal gold metal on the catalyst support surface to form a bimetallic palladium-gold catalyst which provides improved carbon dioxide selectivity and oxygen conversion in vinyl acetate production from ethylene, acetic acid and oxygen.

2. A process in accordance with claim 1 wherein the impregnation of the catalyst support medium in step(1) is conducted with an aqueous solution of a palladium compound, and the palladium compound is fixed on the support medium with an aqueous alkaline solution prior to reduction.

3. A process in accordance with claim 1 wherein the impregnation of the catalyst support medium in step(1) is conducted with an organic solvent solution of an organometallic palladium compound.

4. A process in accordance with claim 1 wherein the organometallic gold compound in step(2) is gold triacetate.

5. A process in accordance with claim 1 wherein the organometallic gold compound in step(2) is dimethyl gold acetate.

6. A process in accordance with claim 1 wherein the organometallic gold compound in step(2) is trimethylsiloxy-dimethyl gold.

7. A process in accordance with claim 1 wherein the organometallic gold compound in step(2) is trimethylsilyl-methyltriphenylphosphine gold.

8. A process in accordance with claim 1 wherein the catalyst product has a palladium metal content between about 0.2–2.5 weight percent, and a gold metal content between about 0.2–2.5 weight percent, based on the catalyst weight.

9. A process in accordance with claim 1 wherein the catalyst support medium is a silica substrate.

10. A process in accordance with claim 1 wherein the catalyst support medium is an alumina substrate.

11. A process in accordance with claim 1 wherein the catalyst product has a palladium:gold weight ration between about 0.5–10:1.

12. A process in accordance with claim 1 where in an additional procedure the catalyst product is impregnated with an aqueous solution of an alkali metal alkanoate activator, and then dried to provide a catalyst product with enhanced selectivity for vinyl acetate production.

13. A process in accordance with claim 12 wherein the activator additive is alkali metal acetate.

14. A catalyst composition for the production of vinyl acetate from ethylene, acetic acid and oxygen, prepared in accordance with the process of claim 1.

15. A heterogeneous bimetallic palladium-gold catalyst composition for the preparation of vinyl acetate from ethylene, acetic acid and oxygen, wherein the catalyst composition comprises a porous catalyst support medium which contains a first shell dispersion coating of colloidal palladium metal on the catalyst support surface, and contains a second shell dispersion coating of colloidal gold metal on the catalyst support surface, said catalyst prepared in accordance with claim 1.

16. A catalyst composition in accordance with claim 15 which has a palladium metal content between about 0.2–2.5 weight percent, and a gold metal content between about 0.2–2.5 weight percent, based on the catalyst weight.

17. A catalyst composition in accordance with claim 15 which has a palladium:gold weight ratio between about 0.5–10:1.

18. A catalyst composition in accordance with claim 15 wherein the catalyst support medium is a silica substrate.

19. A catalyst composition in accordance with claim 15 wherein the catalyst support medium is an alumina substrate.

* * * * *